United States Patent
Funahashi

(10) Patent No.: US 7,053,909 B2
(45) Date of Patent: May 30, 2006

(54) DISPLAY METHOD AND DISPLAY APPARATUS

(75) Inventor: Takeshi Funahashi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 35 days.

(21) Appl. No.: 09/962,128

(22) Filed: Sep. 26, 2001

(65) Prior Publication Data

US 2002/0036645 A1 Mar. 28, 2002

(30) Foreign Application Priority Data

Sep. 26, 2000 (JP) .............................. 2000-292079

(51) Int. Cl.
G09G 5/02 (2006.01)

(52) U.S. Cl. .................. 345/602; 345/549; 345/596; 345/597; 382/132; 382/167; 382/237; 358/3.01; 358/3.06

(58) Field of Classification Search ................ 345/601, 345/602, 596, 597, 549; 382/132, 167

See application file for complete search history.

(56) References Cited

U.S. PATENT DOCUMENTS

| | | | | | |
|---|---|---|---|---|---|
| 5,260,873 A | * | 11/1993 | Hishinuma | .................. | 345/605 |
| 5,384,902 A | * | 1/1995 | Carlsen | ...................... | 345/593 |
| 5,400,053 A | * | 3/1995 | Johary et al. | ............... | 345/691 |
| 5,546,105 A | * | 8/1996 | Leak | ........................... | 345/604 |
| 5,990,864 A | * | 11/1999 | DeAguiar et al. | .......... | 345/600 |
| 6,870,637 B1 | * | 3/2005 | Watanabe | ................... | 358/1.9 |

FOREIGN PATENT DOCUMENTS

JP 11-174992 7/1999

* cited by examiner

Primary Examiner—Matthew C. Bella
Assistant Examiner—Antonio Caschera
(74) Attorney, Agent, or Firm—Sughrue Mion, PLLC

(57) ABSTRACT

The display method and apparatus display colors used in color information on a display unit capable of displaying gray scale. The method and apparatus convert the colors into gray scale values so as to enable differences in the colors to be identified even when the colors are displayed based on the gray scale on the display unit, and then display the color information on the display unit by utilizing the converted gray scale values as the colors. The method and apparatus can recognize meaning of the differences in original colors even in the case of displaying color information on a monochrome display (the display unit capable of displaying the gray scale).

9 Claims, 5 Drawing Sheets

FIG. 2A     FIG. 2B     FIG. 2C
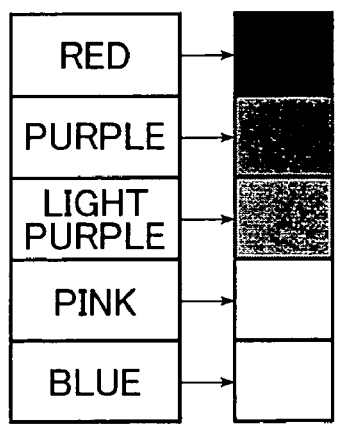 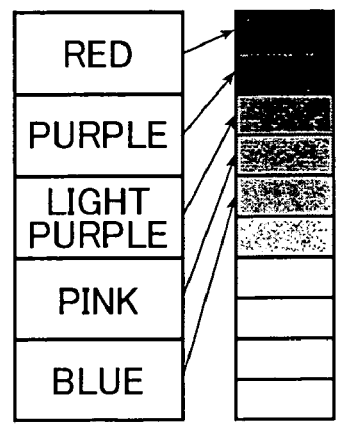 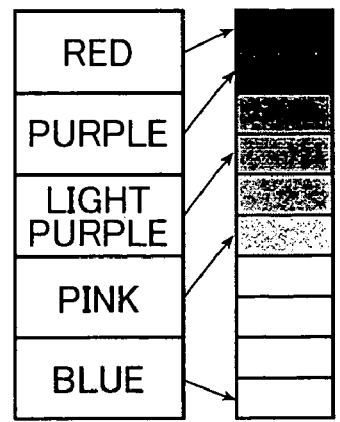
FIG. 2D
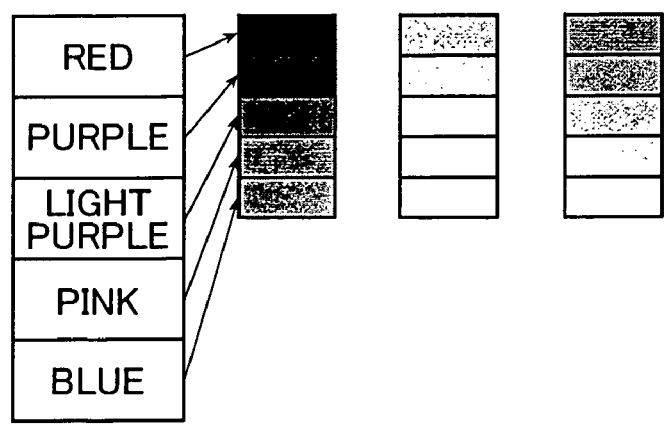

DISPLAY METHOD AND DISPLAY APPARATUS

BACKGROUND OF THE INVENTION

The present invention relates to a display method and a display apparatus, more particularly, to a display method and a display apparatus, in which consideration is given so as to allow recognition of meaning of differences in the original colors even in the case of displaying color information on a monochrome display (a display apparatus capable of displaying a gray scale).

In recent years, a system applying a computer has been constructed in various fields and improvement in work efficiency is being promoted. Similar tendency can be seen in the healthcare field. Establishment of on-line systems for clerical work and data concerning medical care is promoted in medical facilities regardless of the scale, from small clinics to large hospitals. The above data concerning medical care include image data, and a system is established in medical facilities that enables the image data on results of various examinations to be searched and referred to at each computer terminal of the system.

In this case, some problems have been pointed out. One of the problems is that a sense of incongruity arises between a conventional image on a photograph film (hereinafter simply referred to as a film) and a display image on an electronic display apparatus (hereinafter simply referred to as a display apparatus) in a field such as X-ray imaging where recording has been performed by the use of the film and there exists not only a huge storage of data relating to X-ray images recorded on films but also accumulation of many years experience in observation and evaluation thereof (diagnosis by a doctor).

Also, another problem is whether the meaning of the differences in the original colors is identifiable or not in the case of displaying color information (which is not always an image) on a display apparatus for displaying monochrome images such as an X-ray image and capable of displaying a gray scale (in X-ray photographs, an image is recorded on the film using a blue base, but it is essentially a monochrome image). In the following, detailed descriptions will be made for these problems.

First of all, the first case will be described where the image conventionally observed and evaluated as an image on a film is digitalized(electronized? computerized?) by some kind of method and displayed on a display apparatus.

As widely known, in the image recorded on a film, amount of X-ray irradiation (strictly speaking, the amount of the X-ray reaching the film through a subject) and optical density of the film (logarithmic value) are approximately proportional to each other.

In contrast, a direct proportionality within a certain range is generally established between input and output of a display apparatus, so that mere digitalization of the image recorded on a film results in an image which causes the sense of incongruity as described above. Specifically, the proportionality in terms of the logarithmic values is established on one hand, and the direct proportionality is established on the other hand; therefore, the resulting image causes the sense of incongruity to an observer.

To cope with this problem, methods have been proposed in which, when simply digitalizing the image recorded on a film, data conversion is carried out upon displaying the digitalized image on a display apparatus or in which digitalization suitable for displaying on a display apparatus is carried out from the beginning. As a specific example of apparatus embodying the former method, the image display apparatus disclosed in the gazette of JP 11-174992 A can be presented.

Meanwhile, with respect to the problem of identifiability of the differences in the original colors in the case of displaying color information on the display apparatus capable of displaying a gray scale, so much emphasis has not been conventionally placed thereon, and any particular countermeasure has not been suggested. However, with the spread application of color information, it has become indispensable to consider this respect.

SUMMARY OF THE INVENTION

The present invention was made while taking the above-described circumstances into consideration, and an object thereof is to solve the above-described problems seen in the prior art and to provide a display method and a display apparatus, in which consideration is given so as to allow recognition of meaning of differences in original colors, even in the case of displaying color information on a monochrome display (a display apparatus capable of displaying a gray scale).

In order to attain the object described above, the first aspect of the present invention provides a display method, comprising the step of: converting colors used in color information into gray scale values to enable differences in the colors to be identified even when the colors are displayed based on gray scale on a display unit capable of displaying the gray scale; displaying the color information on the display unit by utilizing the converted gray scale values as the colors.

Preferably, the converting step of the color information into the gray scale values is performed with reference to a conversion table.

Preferably, the conversion table uses a part or all of a conversion table prepared as a look-up table in advance in the display unit.

Preferably, the conversion table is created as a look-up table in accordance with the number of the colors of the color information.

Preferably, the conversion table is used by selecting from various kinds of the conversion tables prepared as a look-up table in advance in accordance with the number of the colors of the color information.

In order to attain the object described above, the second aspect of the present invention provides a display apparatus comprising: a display unit capable of displaying a gray scale; a converter for converting colors used in color information into gray scale values to allow differences in the colors to be identified even when displaying is based on the gray scale on the display unit, wherein the color information is displayed by converting the colors used in the color information into the gray scale values by the converter to allow the differences in the colors to be identified even when the colors are displayed based on the gray scale on the display unit.

Preferably, the converter refers to a conversion table.

Preferably, the conversion table uses a part or all of a conversion table prepared as a look-up table in advance.

Preferably, the conversion table is created as a look-up table in accordance with the number of the colors of the color information.

Preferably, the conversion table is used by selecting from various kinds of the conversion tables prepared as a look-up table in advance in accordance with the number of the colors of the color information.

BRIEF DESCRIPTION OF THE DRAWINGS

FIGS. 2A, 2B, 2C and 2D are pattern diagrams each describing an example of LUT data contents in an image display system according to an embodiment.

PREFERRED EMBODIMENTS OF THE INVENTION

Hereinbelow, embodiments of the present invention will be described in detail based on the accompanying drawings.

Figure 1:
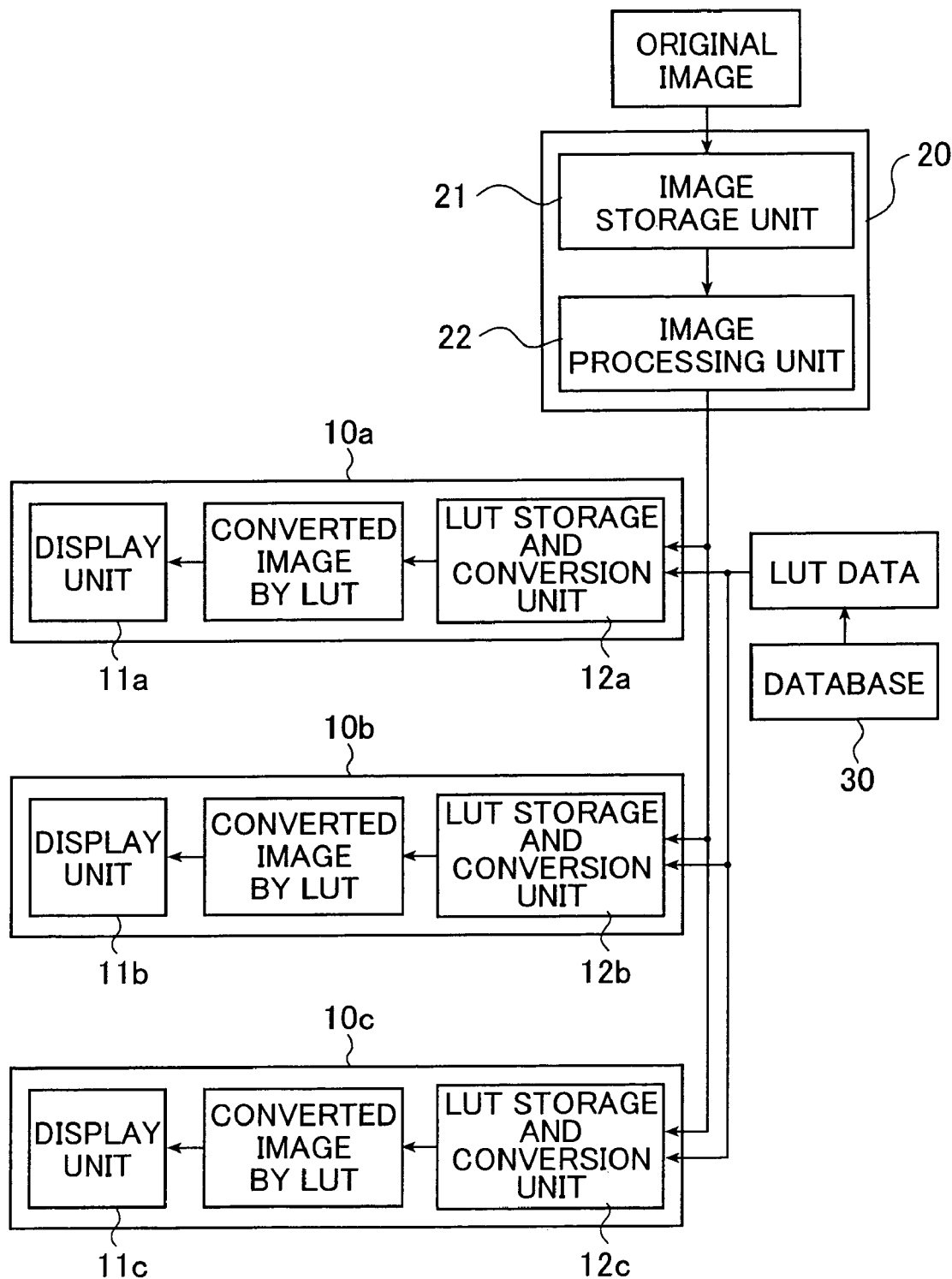
FIG. 1 is a block diagram showing a schematic constitution of an image display system according to an embodiment of the present invention.

FIG. 1 is a block diagram showing a schematic constitution of an image display system according to an embodiment of the present invention. The image display system according to this embodiment is a system for displaying data on a monochrome image of an X-ray photograph and various kinds of examination information accompanying such data (this examination information is character information displayed in color in order to enhance visibility) in an X-ray examination.

Specifically, image data of an X-ray photograph as the main information is usually data on a blue-based monochrome image, and an image display apparatus capable of optimally displaying blue-based monochrome images is selected as an image display apparatus.

On the other hand, various kinds of examination information (character information) as supplementary information are created for color displaying so as to enhance the visibility as described above.

For this reason, various kinds of examination information originally created for color displaying are to be displayed on the image display apparatus for monochrome displaying, thus leading to a situation where various kinds of examination information created for color displaying must be displayed in monochrome. In such a case, as described above, it becomes important to secure identifiability of differences in the original colors of various kinds of examination information created for color displaying.

The above-described differences in the original colors of various kinds of examination information are made to represent various pieces of information such as kind of the examination, date and time of the examination, kind of medical sheet and kind of medicine administered. It is necessary that the image data of an X-ray photograph be observed while taking the above examination information into consideration (observations being done in most cases as image readings by a doctor).

Consequentially, the image display system according to this embodiment is shown in FIG. 1 based on the assumption that image data of a plurality of X-ray photographs are arranged side by side and observed. Specifically, in FIG. 1, reference numerals 10a, 10b and 10c denote flat panel displays of three systems respectively, and the flat panel displays 10a, 10b and 10c are provided with display units 11a, 11b and 11c respectively.

Also, each of the displays 10a, 10b and 10c possesses a conversion function of converting various kinds of examination information created for color displaying as described above, which are included in the image to be displayed on the display unit 11a, 11b or 11c, into the optimal state for monochrome displaying. In this constitution, as described later in detail, the conversion function is such that the conversion can be readily effected by reading a previously prepared conversion table (look-up table, hereinafter referred to as LUT).

Specifically, in the image display system according to this embodiment, a control device 20 is provided, which has an image storage unit 21 and an image processing unit 22 for receiving an image to be displayed from an image supplying unit and for appropriately conducting image processing to supply the image to each of the displays 10a, 10b and 10c. In the image display system, a database 30 is also provided, in which are stored various kinds of LUTs prepared in advance in accordance with the classification of images and the classification of displays.

Here, the contents of LUTs will be described as follows.

Specifically, the LUTs of the image display system according to this embodiment are correspondence tables showing correspondences between the original colors and image densities at the time of monochrome displaying as schematically shown in FIGS. 2A, 2B, 2C and 2D for example. These LUTs are each prepared in advance in accordance with the classification of images and the classification of displays.

Examples shown in FIGS. 2A, 2B, 2C and 2D are made as such described in the following. First, FIG. 2A shows the most common example in which each of the original colors is allocated to a different density in a one-to-one correspondence. FIG. 2B shows an example in which the original colors are allocated to the higher density side, and this example is effective when the image as the main information includes relatively many components with low density.

FIG. 2C shows a unique example in which the original colors are intentionally allocated to densities dispersed within a given range. FIG. 2D shows an example in which the original colors are allocated to densities of four different ranks of density A to D, and selection of a rank from the above ranks is made possible. In this example, it is readily possible to handle such a case where the image as the main information has a wide range of density.

Since the database 30, in which are stored the LUTs constituted as described above, is provided, LUT storage and conversion units 12a, 12b and 12c in the respective displays 10a, 10b and 10c, which possess the conversion function of converting various kinds of examination information created for color displaying into the optimal state for monochrome displaying, perform such conversion operation in a following manner.

Specifically, each of the LUT storage and conversion units 12a, 12b and 12c in the displays 10a, 10b and 10c reads the LUT contents data corresponding to the display unit 11a, 11b or 11c in the display, in which the LUT storage and conversion unit in question is provided, from the above-described database 30 in advance. At the time of the transmission of the image data to be displayed, the LUT storage and conversion units 12a, 12b and 12c select the LUT contents data corresponding to the image data from the abovementioned LUT contents data already read, thus performing the conversion processing.

In accordance with the conversion result, data converted from the one for color displaying into the one for monochrome displaying are transmitted to the display units 11a, 11b and 11c and displayed in a form easy for an observer to see by appropriately superimposing the data on the image data as the main information. In this constitution, various kinds of examination information as supplementary information can be displayed in a form easy for the observer to see without excessively overlapping with the image data as the main information in the range of density.

In the above-described embodiment, a case was described where each of the displays 10a, 10b and 10c reads the LUT contents data corresponding to its own display unit 11a, 11b or 11c from the above-described database 30 in advance. It is also possible to read the LUT contents data from the database 30 at the time of the transmission of the image data to be displayed.

In addition, in the foregoing embodiment, an example was shown where the LUTs for converting data from the one for color displaying into the one for monochrome displaying are stored in the database provided on the control device side (that is, outside each of the displays 10a, 10b and 10c). However, the present invention is not limited to this.

Specifically, the LUTs for converting data from the one for color displaying to the one for monochrome displaying may be stored in a HDD (hard disk drive), a memory card or the like provided inside each of the displays 10a, 10b and 10c. In this case, an effect can be obtained that the processing inside the respective displays 10a, 10b and 10c is sped up.

Figure 3:
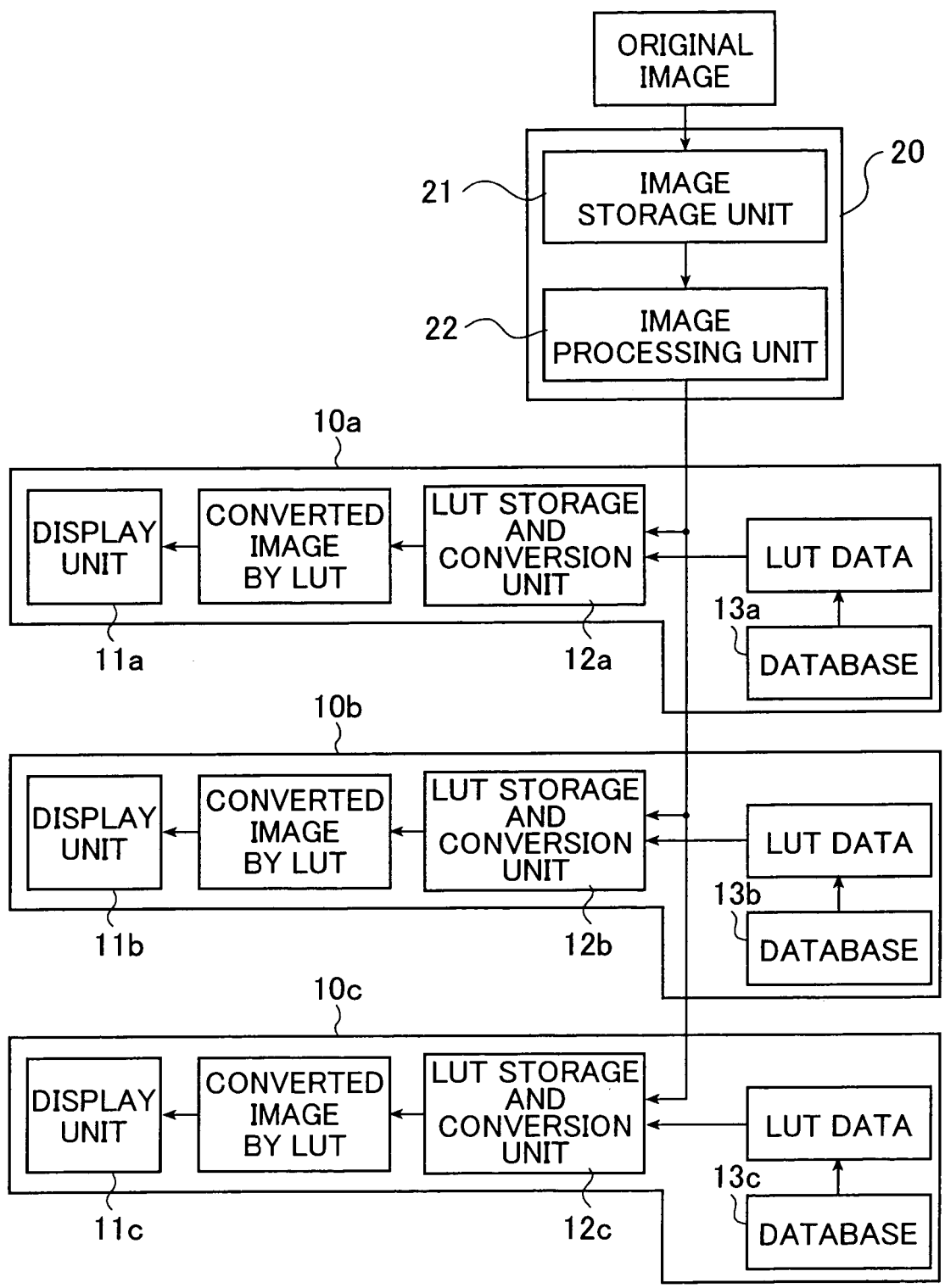
FIG. 3 is a block diagram (part 1) showing a schematic constitution of an image display system according to another embodiment of the present invention.

FIG. 3 shows a constitutional example of such a case. In FIG. 3, reference numerals 13a, 13b and 13c denote LUT databases stored in the HDDs or the memory cards provided inside the displays 10a, 10b and 10c respectively. The effect or the like of this constitution is as described above.

Furthermore, in the image display system according to the present invention, the above-described LUT storage and conversion units 12a, 12b and 12c may be provided all together in the control device 20 instead of inside the respective displays 10a, 10b and 10c. In such a case, the LUT storage and conversion units are preferably disposed individually so as to correspond to the displays 10a, 10b and 10c respectively.

Figure 4:
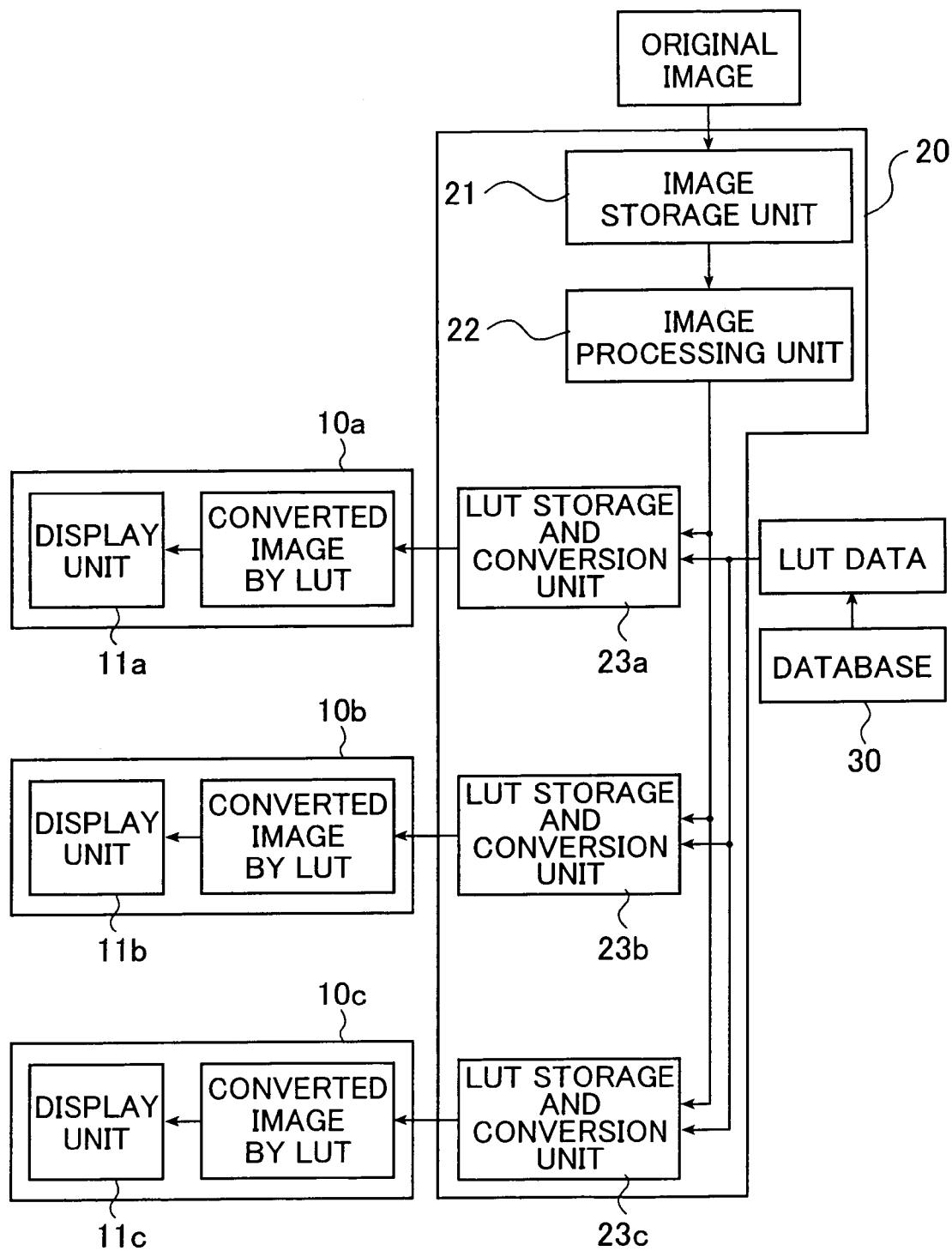
FIG. 4 is a block diagram (part 2) showing a schematic constitution of an image display system according to another embodiment of the present invention.

FIG. 4 shows a constitutional example of such a case. In FIG. 4, reference numerals 23a, 23b and 23c denote the LUT storage and conversion units, which are provided inside the control device 20, corresponding to the displays 10a, 10b and 10c respectively. In this case, the database for storing the LUT data is provided outside the displays 10a, 10b and 10c. The effect or the like of this constitution is as described above.

Figure 5:
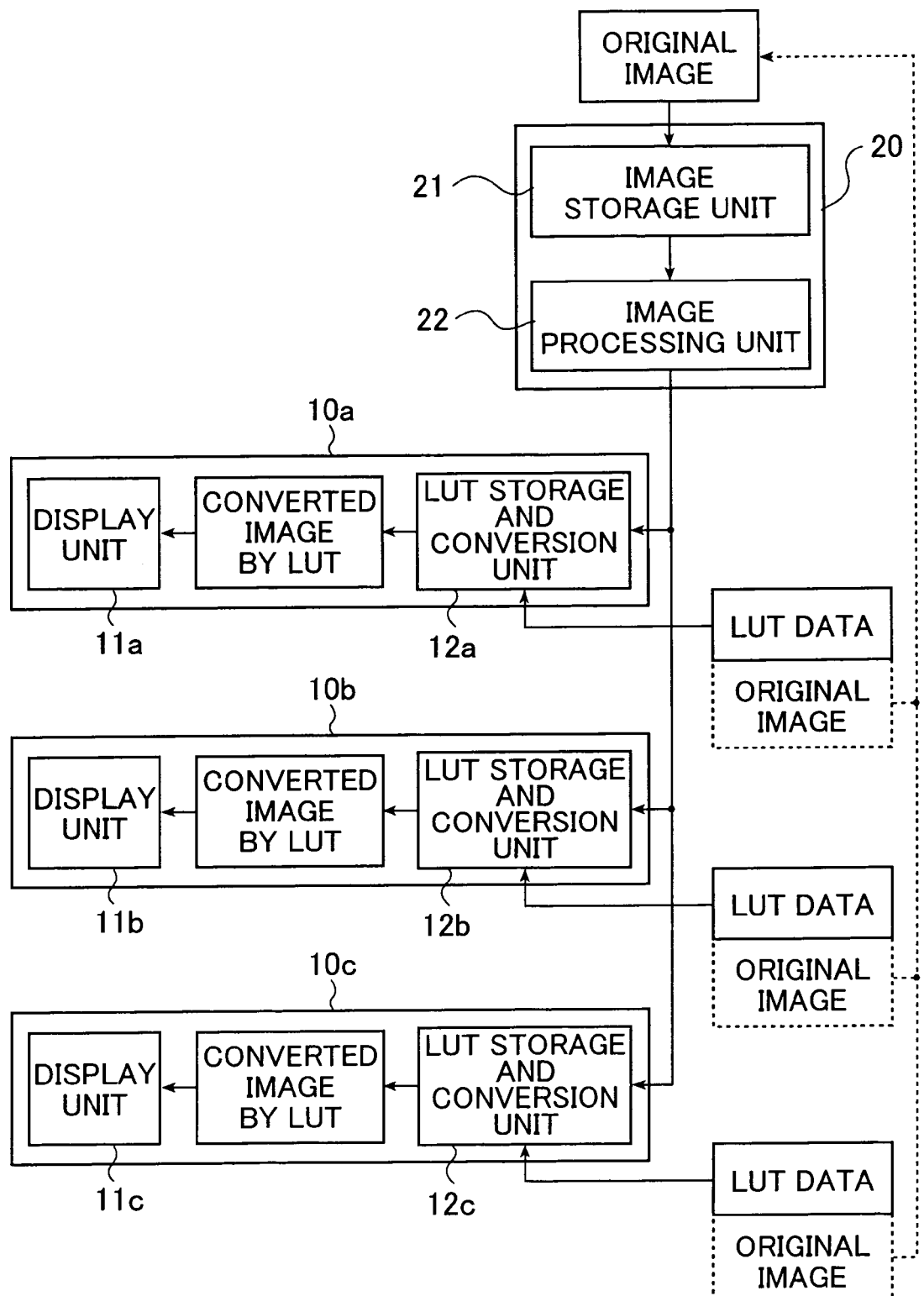
FIG. 5 is a block diagram (part 3) showing a schematic constitution of an image display system according to another embodiment of the present invention.

Still further, the image display system according to the present invention can be constituted such that the LUT data is added to the image data as the main information and supplied from outside without providing the database for storing the LUT data. FIG. 5 shows a constitutional example of such a case. In this case, each of the displays 10a, 10b and 10c will receive and utilize the LUT data corresponding to its own display unit.

The effect in this embodiment is identical to that of the embodiments described above.

Note that each of the foregoing embodiments is shown as an example of the present invention, and it is needless to say that the present invention is not limited to the embodiments.

For example, the image to be displayed is not limited to the image of the X-ray photograph, and other various kinds of monochrome images may be the object to be displayed.

Also, the number of the image display apparatus constituting the system can be determined optionally. In addition, the type of displays used is not limited to the so-called flat panel type, displays of which type include a liquid crystal display apparatus and a plasma display apparatus, and the conventional CRT display apparatus may also be used.

Furthermore, the contents of the LUT data are not limited to those exemplified in FIG. 2, and others of various types can be employed.

As described in detail in the foregoing, according to the present invention, a display method and a display apparatus can be provided, in which consideration is given so as to allow recognition of original colors even in the case of displaying color information on a monochrome display (a display apparatus capable of displaying a gray scale).

More specifically, even in the case where various kinds of examination information originally created for color displaying is displayed on the image display apparatus for displaying monochrome images, meaning of the differences in the original colors can be surely recognized. Therefore, the effect is obtained that the image that is easy for an observer to observe can be displayed.

What is claimed is:

1. A display method, comprising the step of:
    converting colors used in color information into gray scale values to enable differences in the colors to be identified even when said colors are displayed based on gray scale on a display unit capable of displaying said gray scale;
    displaying said color information on said display unit by utilizing said converted gray scale values as said colors;
    wherein said converting step of said color information into the gray scale values is performed with reference to a first conversion table,
    wherein said first conversion table uses a part or all of a second conversion table prepared as a look-up table in advance in said display, and
    wherein said first conversion table is used by selecting from various kinds of conversion tables the second conversion table prepared as a look-up table in advance in accordance with the number of the colors of said color information.

2. The display method according to claim 1, wherein said first conversion table is created as a look-up table in accordance with the number of the colors of said color information.

3. The method of claim 1, wherein the color information comprises color for two or more colors independently.

4. The method of claim 3, wherein each color information is assigned a density range in gray scale.

5. The method of claim 4, wherein three or more colors are represented in density ranges that are non-contiguous.

6. The display method according to claim 1, wherein said display unit is a monochrome display unit.

7. A display apparatus comprising:
    a display unit capable of displaying a gray scale;
    a converter for converting colors used in color information into gray scale values to allow differences in the colors to be identified even when displaying is based on the gray scale on said display unit,
    wherein said color information is displayed by converting said colors used in said color information into the gray scale values by said converter to allow the differences in the colors to be identified even when said colors are displayed based on the gray scale on the display unit;
    wherein said converter refers to a first conversion table,
    wherein said first conversion table uses a part or all of a second conversion table prepared as a look-up table in advance, and
    wherein said first conversion table is used by selecting from various kinds of conversion tables the second conversion table prepared as a look-up table in advance in accordance with the number of the colors of said color information.

8. The display apparatus according to claim 7, wherein said first conversion table is created as a look-up table in accordance with the number of the colors of said color information.

9. The display apparatus according to claim 7, wherein said display unit is a monochrome display unit.

* * * * *